United States Patent [19]

Weigele et al.

[11] Patent Number: 5,516,921
[45] Date of Patent: May 14, 1996

[54] THIONO-LACTONE INHIBITORS OF PROTEIN TRAFFICKING AND USES THEREFOR

[75] Inventors: Manfred Weigele, Cambridge; Mallory F. Loewe, Essex; Christopher S. Poss, Beverly, all of Mass.

[73] Assignee: Ariad Pharmaceuticals, Inc., Cambridge, Mass.

[21] Appl. No.: 308,184

[22] Filed: Sep. 19, 1994

Related U.S. Application Data

[63] Continuation-in-part of Ser. No. 188,083, Jan. 27, 1994, abandoned, Ser. No. 193,820, Feb. 9, 1994, abandoned, Ser. No. 207,319, Mar. 7, 1994, abandoned, and Ser. No. 207,496, Mar. 7, 1994, abandoned.

[51] Int. Cl.$^6$ .................. C07D 313/00; A61K 31/335
[52] U.S. Cl. .................. 549/355
[58] Field of Search .................. 549/355; 514/450

[56] References Cited

PUBLICATIONS

Singleton et al, Nature 181:1072 73(1958).
Pelham, H. R. B., Cell, 67:449 451(1991).
Cheung, P., et al., J. Virol., 65:1893 1904(1991).
Pal, R., et al., Aids Res. Human Retroviruses, 7:707 712(1991).

Primary Examiner—Cecilia Tsang

[57] ABSTRACT

Novel compounds related structurally to Brefeldin A useful as antiviral, antifungal, antiproliferative, immunosuppresive and detoxifying agents as well as pharmaceutical compositions and methods based thereon are disclosed.

3 Claims, No Drawings

THIONO-LACTONE INHIBITORS OF PROTEIN TRAFFICKING AND USES THEREFOR

This application is a continuation-in-part of U.S. Ser. Nos. 08/188,083 (filed Jan. 27, 1994) now abandoned, 08/193,820 (filed Feb. 9, 1994) now abandoned, 08/207,319 (filed Mar. 7, 1994) now abandoned and 08/207,496 (filed Mar. 7, 1994) now abandoned, the contents of each of which are incorporated herein by reference.

BACKGROUND

Brefeldin A (decumbin, "BFA") was first isolated in 1958 as a fungal metabolite from Penicillium decumbens (Singleton, V. L., et al., Nature 181:1072–1073 (1958)). BFA has a molecular weight of 280.37 ($C_{16}H_{24}O_4$) and reportedly has a wide range of biological activities, including antifungal, antiviral and antitumor effects. See Betina, Folia Microbiol. 37(1):3–11 (1992) for a recent review. At the cellular level, BFA has dramatic effects on the secretory pathway and protein trafficking in mammalian cells. (Pelham, H. R. B., Cell, 67:449–451 (1991); (Klausner, R. D., et al., J. Cell Biol., 116:1071–1080 (1992)). BFA has been shown to also inhibit protein transport in fungi, such as *Candida albicans* (Arioka, M., et al., J. Gen. Microbiol., 137:1253–1262 (1991)) and inhibit the presentation of endogenous and exogenous protein antigens by MHC class II-restricted T-cells (Adorini, L., et al., Nature, 246:63–66 (July 1990)). BFA has also been shown to have selective cytotoxic activity against human tumor cell lines (Ishii, S., et al., J. Antibiot., XLII:1877–1878 (1989)).

BFA also inhibits virus replication by interfering with the intracellular transport and maturation of viral proteins. Inhibition, as defined herein, means a significant reduction in virus particle replication, as well as complete abrogation of virus particle replication. Enveloped viruses, such as herpes viruses (including Herpes Simplex) and Human Immunodeficiency Virus (HIV), require the host cell secretory apparatus for transport and processing of envelope (membrane) glycoproteins during the course of virus assembly and maturation. BFA has also been shown to inhibit infectious viral particle formation by preventing the transport of envelope glycoprotein to the cell surface as required for assembly of mature, infectious viral particles. (Cheung, P., et al., J. Virol., 65:1893–1904 (1991); Pal, R., et al., Aids Res. Human Retroviruses, 7:707–712 (1991); see also Takatsuki et al, Agric. Biol. Chem. 49(3):899–902 (1985)).

BFA has a short biological half-life. It is rapidly deactivated in vivo via conjugation with glutathione by glutathione S-transferase and subsequently transported out of the cell (Bruning, A., et al., J. Biol. Chem., 267:7726–7732 (1992)). Compounds having some or all of the biological activities of BFA combined with an extended useful biological half-life and/or improved overall therapeutic profiles would be valuable for the treatment of viral, bacterial, fungal and other diseases, as anti-cancer agents, as immunosuppresive agents and as detoxifying agents.

DESCRIPTION OF THE INVENTION

This invention concerns novel compounds related structurally to Brefeldin A; methods of synthesizing these compounds; use thereof as antiviral, antifungal, detoxification and antiproliferative agents (e.g., antitumor agents and agents to treat genital warts); pharmaceutical compositions which contain these compounds as active components; and pharmaceutical methods involving administration of these compounds to mammals, preferably human patients, in need thereof. These compounds block, or inhibit, the transport of proteins from the endoplasmic reticulum (ER) and through the Golgi apparatus in a cell and are also useful as experimental research reagents.

This invention encompasses compounds of the formula:

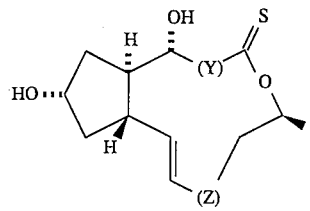

wherein Y is a trans unsaturated 2-carbon unit or a fused cyclopropyl ring, i.e., Y is

and Z is an unsaturated 2-carbon unit (cis or trans), or a hydroxy- or fluoro-substituted saturated 2-carbon unit, i.e., Z is

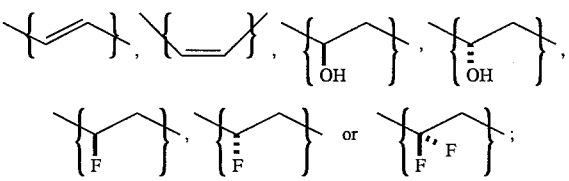

as well as their isolated diastereoisomers, diastereomeric mixtures and esters thereof.

Illustrative compounds in which Y is a trans double bond include the following:

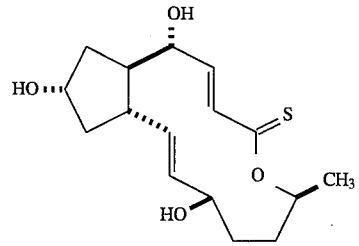

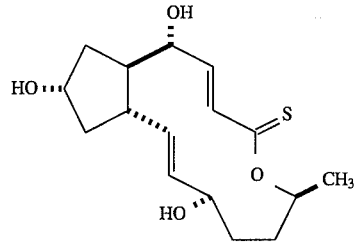

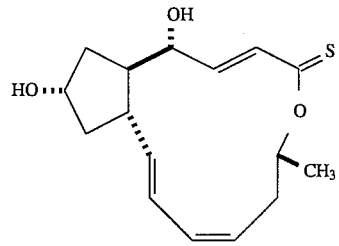

-continued

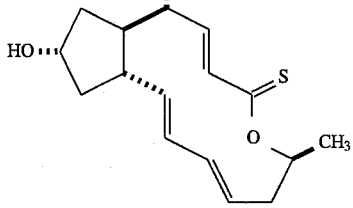

Illustrative compounds in which Y is a cyclopropyl ring include the following:

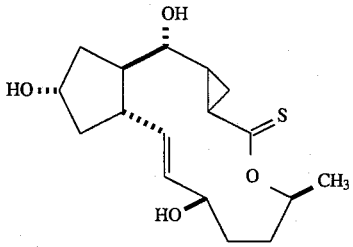

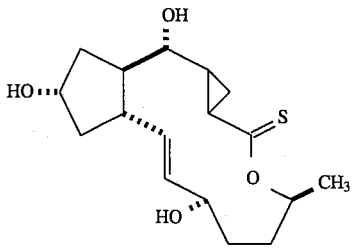

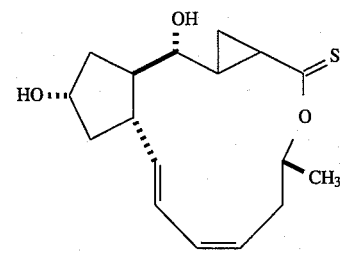

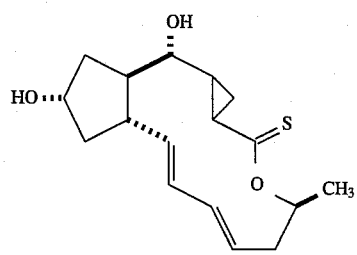

The cyclopropyl ring junctions may have either R,R or S,S stereochemical configuration.

The esters mentioned above include, among others, compounds of this invention in which one or more of the hydroxyl groups bear acyl moieties of the formula $R^1CO$— where $R^1$ is —$(CH_2)_n$—Y, where n is an integer from 2 through about 6 and Y is —$CO_2H$, $SO_3H$, $PO_3H$, amino, alkylamino, dialkylamino or trialkylammonium and pharmaceutically acceptable salts thereof. The alkyl groups may be the same or different and may be substituted or unsubstituted and may be straight-chain, branched or cyclic. For example, alkyl substituents include saturated straight-chain, cyclic or branched hydrocarbon moieties, preferably of one to about twelve carbon atoms, including methyl, ethyl, n-propyl, i-propyl, cyclopropyl, n-butyl, i-butyl, t-butyl, cyclobutyl, cyclopropylmethylene, pentyl, hexyl, heptyl, octyl and so forth, and may be optionally substituted with one or more substituents such as lower alkoxy, carboxy, amino, phenyl, aryl, mercapto, halo (fluoro, chloro, bromo or iodo), azido and cyano. See e.g. U.S. Ser. Nos. 08/207,319 and 08/207,496, supra.

An illustrative example of such an ester, where $R^1$ is (COOH)—$CH_2CH_2$—CO—, is depicted below:

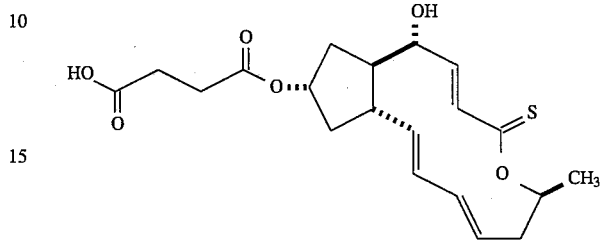

The compounds of this invention can be used as biological reagents to inhibit the intracellular transport of proteins from the ER of a cell through the compartments of the Golgi apparatus, and, ultimately, to the cell surface. For example, the compounds of this invention can be used to inhibit maturation of viral membrane glycoproteins in a cell infected with a virus by inhibiting the transport of viral membrane glycoproteins from the ER of the cell through the compartments of the Golgi apparatus, and, ultimately, to the cell surface, as required for the assembly of mature, infectious virus particles. These compounds can likewise be used to inhibit the transport, and thus the otherwise concomitant processing and presentation, of antigens by antigen presenting cells.

Compounds of this invention can also be used in pharmaceutical applications as antiviral, antifungal, immunosuppressive and antiproliferative agents (e.g., antitumor and anti-wart agents) and as detoxification agents. Accordingly, this invention further relates to pharmaceutical compositions which contain as active components compounds described herein which are effective for one or more of the indications noted herein and which can be administered to an individual in need thereof. For example, a compound of this invention can be combined with a physiologically compatible carrier for administration to an individual infected with a fungus or virus, or to an individual harboring a tumor. Without wishing to be bound by a particular theory, we do note that the compounds of this invention may act, at least in part, by inhibiting the transport of proteins critical, for example, to the maturation, intracellular replication and/or infectivity of virus, to the growth and/or proliferation of tumor cells, or to fungal growth.

SYNTHESIS

The thiono-lactones of this invention can be produced synthetically from BFA or other lactone derivatives of BFA using Lawesson's reagent as described in detail below. BFA can be prepared by fermentation followed by product recovery from the culture medium as described in detail in Harri, E., et al., Helv. Chim. Acta, 46:1235 (1963). Alternately, BFA can be synthesized using standard laboratory methods. (Baudouy, R., et al., Tetrahedron Letters, 34:2973–2976 (1977); LeDrian, C., et al., J. Am. Chem. Soc., 104:5473–5483 (1982); Kitahara, T. and Mori, K., Tetrahedron, 40:2935–2944 (1984)). BFA can then be transformed to produce the compounds described herein as described in the Examples which follow.

Another starting material is the cyclopropyl analog of BFA illustrated by formula (II):

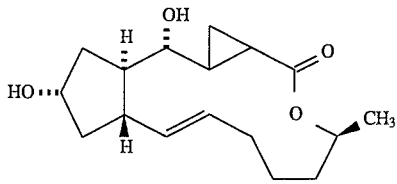

which can be synthesized by reacting BFA with a slurry of trimethylsulfoxonium iodide, dimethyl sulfoxide and pentane-washed sodium hydride. An illustrative procedure is provided in Example 4. The method of synthesis described herein results in a mixture of two diastereomers. Under the conditions described in the examples which follow, the 2R, 3R-diastereomer is the major product. The two diastereomers can be separated by standard laboratory methods. In addition, the apex of the cyclopropyl ring can be further modified to include one or two, halogens (e.g., fluoride), or, alternately, one, or two, unbranched alkyl groups. It should also be noted that the corresponding esters of the compounds disclosed herein (which esters are also encompassed by this invention and may be used for the purposes disclosed herein) can be prepared prior to or following final deprotection of the thiono-lactones. See e.g. U.S. Ser. Nos. 08/207,319 and 08/207,496, supra.

Flouro and di-fluoro compounds of this invention can be prepared from the corresponding hydroxy (with stereochemical inversion) and keto compounds, respectively, (typically with protection of other hydroxy groups and subsequent deprotection) using diethylaminosulfur trifluoride (DAST). See e.g. Middleton et al, J Fluorine Chem (1983) 23:557 (conversion of hydroxyl to fluoro); Middleton et al, J Fluorine Chem (19800 45:2883 (conversion of keo to difluoro); and M. Hudlicky, Organic Reactions (1988), vol 35, pp. 513 et seq (review).

EVALUATION OF IN VITRO BIOLOGICAL ACTIVITY

The biological activity of these compounds can be evaluated and compared using conventional in vitro assays for inhibition of protein trafficking between the endoplasmic reticulum (ER) and the Golgi apparatus and specifically for antiviral, antitumor, immunosuppressive and antifungal activity as discussed in further detail below.

(a) Inhibition of Protein Transport

The inhibitory activity of the compounds with respect to protein transport can be evaluated in a cell-free system as described in Orci, L., et al., Cell, 64:1183–1195 (1991). Generally, secretory proteins, such as membrane glycoproteins, are transported from the endoplasmic reticulum to the Golgi apparatus, and subsequently to the cell surface, via transport vesicles. To evaluate the ability of the compounds described herein to prevent the formation of transport vesicles, Golgi apparatus membranes can be isolated and incubated with cytosol, ATP, an ATP regenerating system and the compounds to be tested as described in Orci, L., et al., Cell, 64:1183–1195 (1991).

The activity of our compounds in inhibiting protein transport may also be evaluated using a Guanine Nucleotide Exchange Factor (GEF) assay as described in detail in the Examples. The GEF assay is based on assays described in Donaldson, J. G., et al., Nature, 360:350–352 (1992), and Helms, J. B., et al., Nature, 360:352–354 (1992). A number of cytosolic proteins are specifically associated with the Golgi apparatus. One such protein, β-COP, is rapidly released from the Golgi upon treatment with BFA. This release occurs within 20 seconds of BFA treatment and is complete in 1–2 minutes. Upon removal of BFA, β-COP rapidly reassociates with the Golgi apparatus. (Klausner, R. D., et al., J. Cell Biol. 116:1071–1080 (1992)). The binding of β-COP to Golgi membranes has been shown to be dependent on the interaction of another protein, ADP-ribosylation factor (ARF) with the Golgi membrane. ARF association with the Golgi is, in turn, dependent on binding the guanine nucleotide, GTP. A component of Golgi membranes specifically catalyzes the exchange of GTP onto ARF. BFA prevents the assembly of β-COP onto the Golgi membrane by inhibiting the GTP-dependent interaction of ARF with the Golgi membrane. (Donaldson, J. G., et al., Nature, 360:350–352 (1992); Helms, J. B., et al., Nature, 360:352–354 (1992)).

The activity of our compounds in preventing Golgi membranes from catalyzing the exchange of GTP onto ARF may be evaluated as described in the Examples below.

(b) Anti-viral Activity

BFA has been shown to have dramatic effects on membrane protein glycosylation and processing, key steps which affect the egress of enveloped viruses from infected cells. (Whealy, M. E., et al., J. Virol., 65:1066–1081 (1991)). The envelopment of a virus, during the maturation process in an infected host cell, appears to be a multistep pathway. The viral capsid acquires a membrane by budding of the capsid through the nuclear membrane such that an immature enveloped virion is formed. This immature virion is transported through the endoplasmic reticulum (ER) and undergoes subsequent de-envelopment, with release of the immature virus particle in proximity to the Golgi apparatus. Subsequent maturation of the immature virion occurs at the Golgi apparatus, which involves a second envelopment of these immature capsids by membrane proteins derived from the Golgi apparatus, containing fully processed viral glycoproteins. The resulting mature, infectious enveloped virus particle is released from the cell by fusion of the outer membrane of the virion envelope with the plasma membrane of the host cell, or, alternately, can be transported via transport vesicles to the cell surface, where membrane fusion results in presentation of viral glycoproteins on the cell surface. BFA does not affect protein synthesis at the translational level, but blocks the post-translational processing and export of viral glycoproteins to the Golgi apparatus, thus, inhibiting viral replication by preventing the formation and/or release of mature, infectious virus particles.

The compounds of this invention can be tested for specific antiviral activity as described in Example 7 as well as by other conventional antiviral assay methods. See e.g. Whealey et al, supra; Johnson et al, J Virol 43(3):1102–1112 (1982); Sidwell et al, Nucleotides and Nucleosides 8:833–836 (1989) and Chen et al, J Virol 65(3):1427–1439 (1991). As described in detail in Example 7 the antiviral activity and non-specific cytotoxic effects of these compounds can be readily evaluated using Hep2 cells infected with Herpes Simplex Virus type 1 (HSV-1). BFA can be used as a control, as can clinically relevant or other known positives, such as IUDR (iodouracyl deoxyribocyte) which can be used as an antiviral, positive control.

(c) Evaluation of Other in vitro Activities

Compounds can be evaluated with respect to specific antifungal, anticancer, immunosuppressive or other pharmaceutically relevant activities using conventional materials and methods. See e.g. Arioka, J. Gen. Microbiol., 137:1253–1262 (1991) (evaluation of antifungal activity); Ishii et al, J. Antibiot. XLII:1877–1878 (1989) (evaluation of cytotoxic/antitumor activity); Sun et al, U.S. Pat. No. 5,206,249 (Apr. 27, 1993)(evaluation of in vitro growth inhibitory activity on cultured leukemia cells); and Yoshida et al, Experimental Cell Research 192:389–395 (1991)(evaluation of anti-toxin activity).

EVALUATION OF IN VIVO BIOLOGICAL ACTIVITY

Bioactivity can be further evaluated in conventional animal model systems including anti-viral, anti-fungal, antitumor, immunosuppression and detoxification assays involving experimental animal models, e.g. using rats, mice, rabbits, guinea pigs, sheep or non-human primates. Numerous animal models for such studies, as well as animal models for determining biological half-life, pharmacokinetics and toxicology, are well known in the art. In vivo toxicity can be readily evaluated with conventional toxicity assays as well as by the method described in Example 8.

(a) in vivo antiviral activity

The effectiveness of the compounds of this invention in controlling viral infection can be evaluated in any of the conventional assay systems. See e.g. Stanberry, "Pathogenesis of Herpes Simplex Virus Infection and Animal Models for its Study" and Renegar, Laboratory Animal Science 42(3):222. For instance, HSV infection can be evaluated using guinea pig and mouse model systems that are art-recognized models used in the study of genital herpes. The guinea pig model system is described in detail in Stanberry, L. R., et al., J. Infect. Diseases, 153:1055–1061 (1986), and Bourne et al, Antimicrob. Agents and Chemo., 36:2020–2024 (1992). The effectiveness of antiviral agents against influenza virus can be evaluated in mice as described by Sidwell et al, in Antiviral Res. 6:343–353 (1985) and Antimicrob. Ag. Chemother. 36:473–476 (1992).

(b) in vivo antitumor activity

The antitumor effectiveness of our compounds can be evaluated in vivo with conventional xenograft models using various human tumor cell lines xenografted into mice as described, for example, in Sun et al, supra, as well as in various transgenic animal models (again, see Sun et al, col 21).

PHARMACEUTICAL APPLICATIONS

Compounds of this invention which prevent, inhibit or reduce the severity of viral infection (e.g. an infection by a virus such as a Herpes Simplex virus), fungal infection (e.g. an infection by a fungus such as Candida albicans), tumors or tumor growth or the effect of toxic substances or which have an immunosuppressive effect may be used in pharmaceutical compositions and methods for treatment or prevention in a mammal in need thereof.

Mammals include rodents such as mice, rats and guinea pigs as well as dogs, cats, horses, cattle, sheep, non-human primates and humans.

The preferred method of such treatment or prevention is by administering to a mammal an effective amount of a compound of this invention to prevent, alleviate or cure said disease or disorder. An effective amount of a compound of this invention is an amount of one or more compounds of this invention which inhibits one or more of protein transport from the endoplasmic reticulum, viral replication, fungal growth, tumor cell growth and pathological effect(s) of a toxin, or which results in immunosuppression, as the case may be. Such effective amounts can be readily determined by evaluating the compounds of this invention in conventional assays well-known in the art, including assays described herein.

Therapeutic/Prophylactic Administration & Pharmaceutical Compositions

The invention provides methods of treating, preventing and/or alleviating the symptoms and/or severity of a disease or disorder referred to above by administration to a subject a compound of the invention in an amount effective therefor. The subject will be an animal, including but not limited to animals such as cows, pigs, chickens, etc., and is preferably a mammal, and most preferably human.

Various delivery systems are known and can be used to administer a compound of this invention, e.g., encapsulation in liposomes, microparticles, microcapsules, etc. One mode of delivery of interest is via pulmonary administration, as detailed more fully infra. Other methods of introduction include but are not limited to intradermal, intramuscular, intraperitoneal, intravenous, subcutaneous, intranasal, epidural and oral routes. A compound of this inventions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary infections or tumors, preferred routes of administration are oral, nasal or via a bronchial aerosol or nebulizer.

In specific embodiments, it may thus be desirable to administer a compound of this invention locally to the area in need of treatment; this may be achieved by, for example, and not by way of limitation, local infusion during surgery, topical application (e.g., for viral or fungal infections or tumors of the skin), by injection, by means of a catheter, by means of a suppository, or by means of a skin patch or implant, said implant being of a porous, non-porous, or gelatinous material, including membranes, such as sialastic membranes, or fibers.

This invention also provides pharmaceutical compositions. Such compositions comprise a therapeutically (or prophylactically) effective amount of a compound of this invention, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of one or more of the compounds described herein can also be accomplished topically by administering the compound(s) directly to the affected area of the skin of the individual. For this purpose, the compounds are administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as antioxidants, humectants, viscosity stabilizers, and similar agents may be added as necessary.

In addition, in certain instances, it is expected that the compounds of this invention may be disposed within devices placed upon, in, or under the skin. Such devices include patches, implants, and injections which release the compound into the skin, by either passive or active release mechanisms.

In a specific application of this invention, we note that genital infection with HSV is characterized by herpetic lesions on the external genital skin. As a consequence of initial genital infection, latent infection is established. One possible mechanism for the maintenance of latency involves the migration of virus from recurrent lesions back to sensory ganglia, where a new set of neurons are infected and become a source of latent virus responsible for recurrent disease. (Stanberry, L. R., et al., J. Infect. Dis., 153:1055–1061 (1986)). Thus, administration of an antiviral agent which inhibits the formation of mature infectious virus particles would be useful to prevent migration of HSV and reasonably prevent establishment of a latent HSV infection. Topical administration of a compound of this invention directly to the areas of the skin affected with the herpetic lesions would be an attractive method of administration. As an illustrative example of anti-viral application of a pharmaceutical agent, see Whitley et al, "Acyclovir: A Decade Later", New England Journal of Medicine pp. 782–789 (Sep. 10, 1992).

Materials and methods for producing the various formulations are well known in the art [see e.g. U.S. Pat. Nos. 5,182,293 and 4,837,311 (tablets, capsules and other oral formulations as well as intravenous formulations)].

A compound of this invention can be formulated in neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2- ethylamino ethanol, histidine, procaine, etc.

The effective dose of compounds of this invention will typically be in the range of about 0.01 to about 50 mg/kgs, preferably about 0.1 to about 10 mg/kg of mammalian body weight, administered in single or multiple doses. Generally, the compounds of this invention may be administered to patients in need of such treatment in a daily dose range of about 1 to about 2000 mg per patient.

The amount of a compound of this invention which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level of our compounds, as the active component(s), should be determined by the attending physician or other health care provider and will depend upon well known factors, including route of administration, biological activity of the particular compound, and the age, body weight, sex and general health of the individual; the nature, severity and clinical stage of the disease; and the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Pulmonary Administration

In an embodiment of this invention of particular interest, a compound of this invention is administered by pulmonary administration, e.g. via aerosolization. This route of administration may be particularly useful for treatment or prophylaxis of bronchial or pulmonary infection or tumors.

Pulmonary administration can be accomplished, for example, using any of various delivery devices known in the art (see e.g., Newman, S. P., 1984, in Aerosols and the Lung, Clarke and Davia (eds.), Butterwarths, London, England, pp. 197–224; PCT Publication No. WO 92/16192 dated Oct. 1, 1992; PCT Publication No. WO 91/08760 dated Jun. 27, 1991; NTIS Patent Application 7-504-047 filed Apr. 3, 1990 by Roosdorp and Crystal), including but not limited to nebulizers, metered dose inhalers, and powder inhalers. Various delivery devices are commercially available and can be employed, e.g., Ultravent nebulizer (Mallinckrodt, Inc., St. Louis, Mo.); Acorn II nebulizer (Marquest Medical Products, Englewood, Colo.), Ventolin metered dose inhaler (Glaxo Inc., Research Triangle Park, N.C.); Spinhaler powder inhaler (Fisons Corp., Bedford, Mass.) or Turbohaler (Astra). Such devices typically entail the use of formulations suitable for dispensing from such a device, in which a propellant material may be present.

Ultrasonic nebulizers tend to be more efficient than jet nebulizers in producing an aerosol of respirable size from a liquid (Smith and Spino, "Pharmacokinetics of Drugs in Cystic Fibrosis," Consensus Conference, Clinical Outcomes for Evaluation of New CF Therapies, Rockville, Md., Dec. 10–11, 1992, Cystic Fibrosis Foundation).

A nebulizer may be used to produce aerosol particles, or any of various physiologically acceptable inert gases may be used as an aerosolizing agent. Other components such as physiologically acceptable surfactants (e.g., glycerides), excipients (e.g., lactose), carriers, and diluents may also be included.

This invention is not to be limited in scope by the specific embodiments described herein. Indeed, various modifications of the invention in addition to those described herein will become apparent to those skilled in the art from the foregoing description. Such modifications are intended to fall within the the scope of the appended claims.

Various patents, patent applications and publications are cited herein, the disclosures of which are incorporated by reference in their entireties.

EXAMPLES

Example 1. Thiono-Brefeldin A

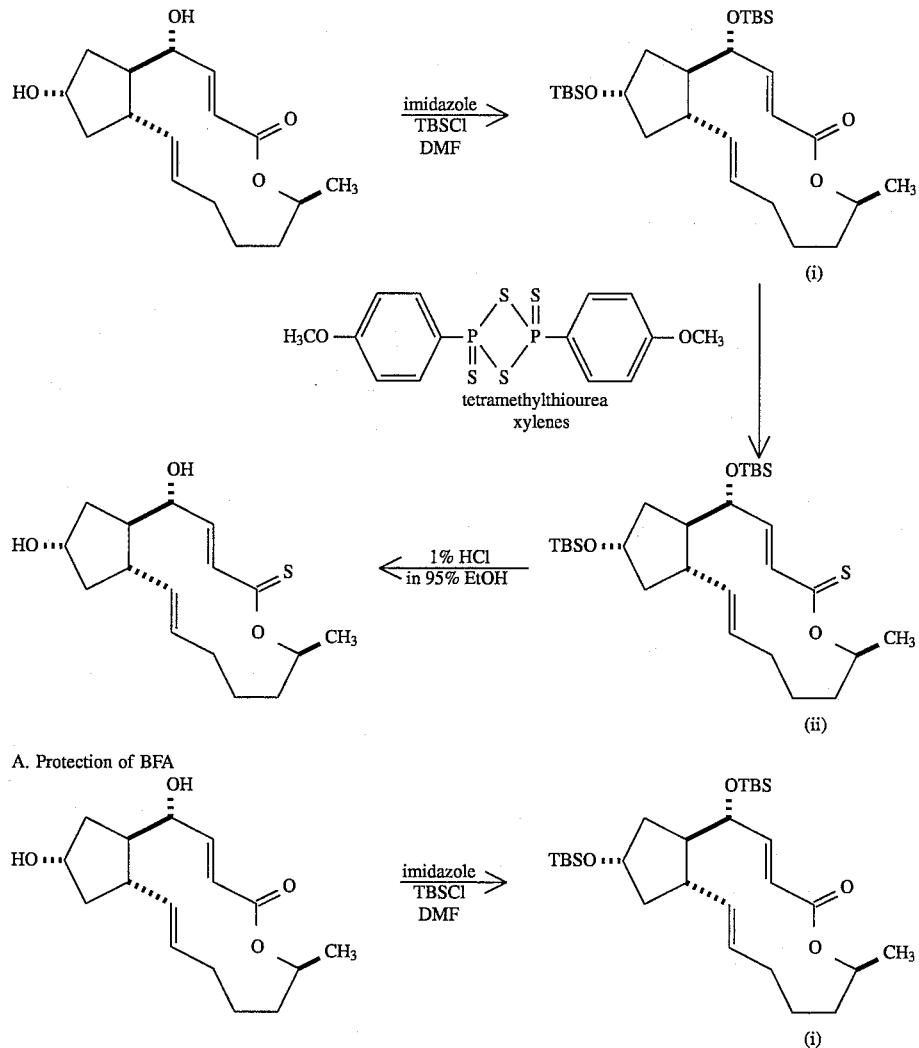

A. Protection of BFA

To a magnetically stirred solution of brefeldin A (2.0 g, 7.1 mmol) in 10 mL N,N-dimethylformamide was added imidazole (1.2 g, 17 mmol) and tertbutyldimethylsilyl chloride (2.4 g, 16 mmol). The reaction was stirred at room temperature for 18 h, then diluted with ethyl acetate and washed with $H_2O$ (2×) and brine. The organic layer was dried over $MgSO_4$, filtered, and concentrated. The crude product was purified via flash chromatography (5% ethyl acetate in hexanes) to provide 3.6 g (quantitative yield) of lactone (i) as an amorphous white solid. $^1H$ spectra of (i) agreed with the proposed structure.

B. Conversion to thiono-lactone

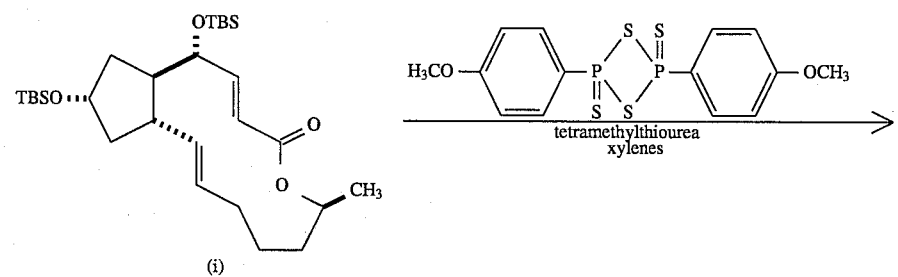

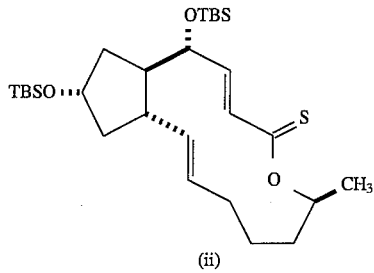

(ii)

To a magnetically stirred solution of protected lactone (i) (3.6 g, 7.1 mmol) in 50 mL of xylenes in a sealed tube was added Lawesson's reagent (5.7 g, 14 mmol) and 1,1,3,3-tetramethyl-2-thiourea (1.9 g, 14 mmol). The reaction tube was sealed, warmed to 170° C., and stirred at this temperature for 2 h. The reaction was allowed to cool to room temperature and the solids filtered off before concentrating. The crude product was purified via flash chromatography (5% ethyl acetate in hexanes) to provide a somewhat impure yellow oil. The crude oil was then re-purified via flash chromatography (2.5% ethyl acetate in hexanes) to provide 1.3 g (35% yield) of protected thiono-lactone (ii) as a yellow oil. $^1$H spectra of (ii) agreed with the proposed structure.

c. Deprotection of thiono-lactone

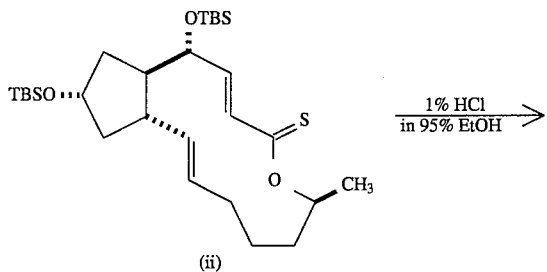

(ii)

-continued

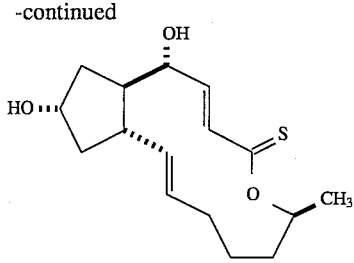

To a magnetically stirred solution of thiono-lactone (ii) (1.3 g, 2.5 mmol) in 20 mL of 1% HCl in 95% ethanol was stirred at room temperature for 20 h. The reaction was quenched with solid NaHCO$_3$, filtered, and concentrated. The crude product was purified via flash chromatography (ethyl acetate) to provide 407 mg (55% yield) of a yellow solid. $^1$H NMR agreed with the proposed structure. Single-crystal X-ray analysis of the product independently confirmed the structure as thiono-brefeldin A.; HRMS (EI$^+$) calcd for C$_{16}$H$_{24}$O$_3$S: 296.1446, found 296.1440.

Example 2. Preparation of (12R)-OH BFA by the following route:

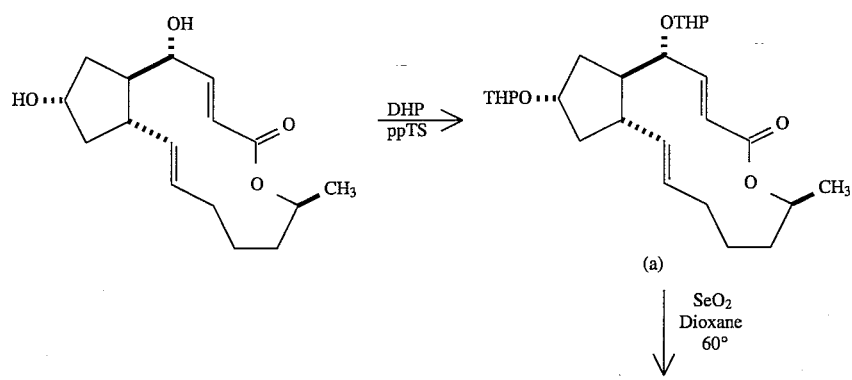

(a)

SeO$_2$
Dioxane
60°

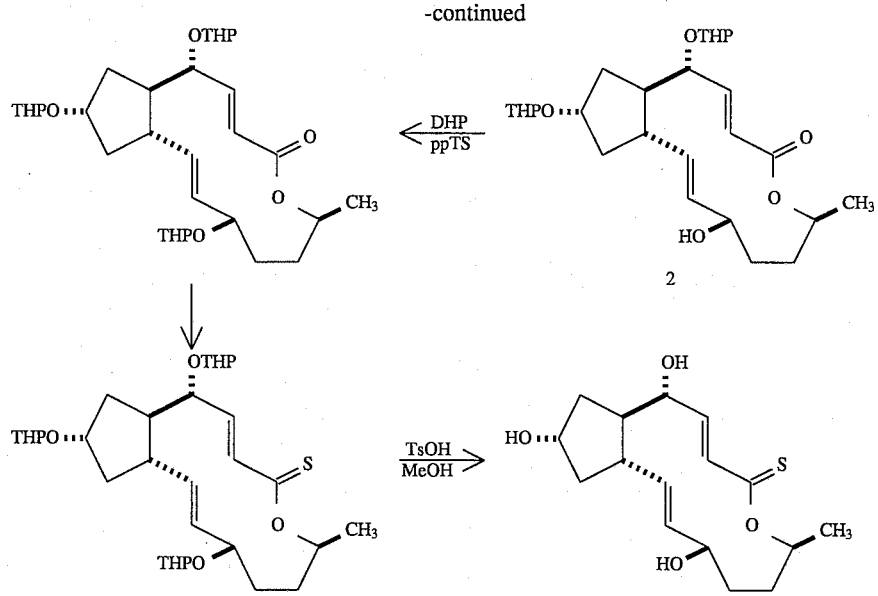

A. Di-THP BFA

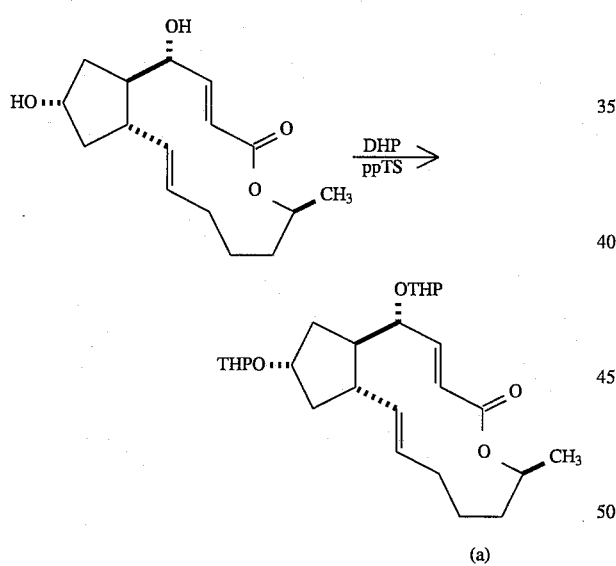

To a magnetically stirred solution of brefeldin A (2.0 g, 7.1 mmol) in 100 mL CH$_2$Cl$_2$ was added 3,4-dihydro-2H-pyran (2.8 mL, 30.7 mmol) and pyridinium toluene-p-sulphonate (10 mg, 0.04 mmol). The reaction was stirred at room temperature for 16 h, then diluted with CH$_2$Cl$_2$ and washed with saturated aqueous NaHCO$_3$ and brine. The organic layer was dried over MgSO$_4$, filtered, and concentrated to afford 3.2 g (quantitative yield) of bistetrahydropyranyl protected brefeldin A (a). Compound (a) was judged sufficiently pure by $^1$H NMR analysis to be used in the subsequent reaction without further purification.

B. Hydroxylation

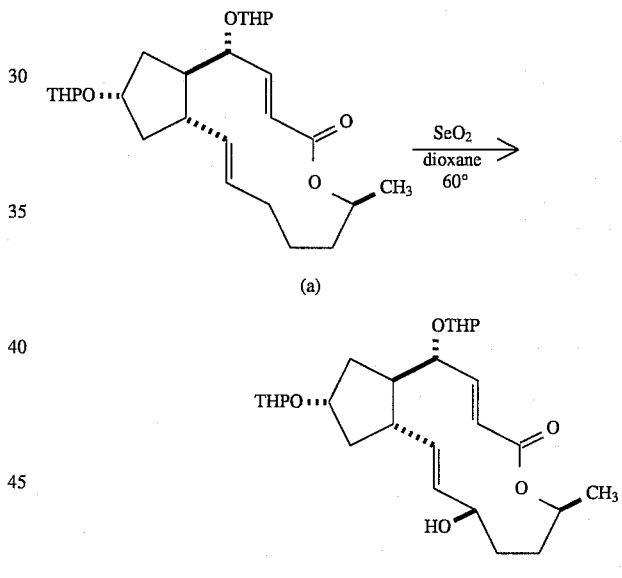

To a magnetically stirred solution of protected brefeldin A (a) (3.2 g, 7.0 mmol) in 60 mL of 1,4 dioxane was added selenium dioxide (1.6 g, 14 mmol). The mixture was warmed to 60° C. and stirred at this temperature for 48 h. The reaction was allowed to cool to room temperature and stirred another 24 h. The suspension was filtered through celite, washing with EtOAc. The flitrate was diluted with more EtOAc and washed with saturated aqueous NaHCO$_3$ and brine. The organic layer was dried over MgSO$_4$, filtered, and concentrated. The crude product was purified via flash chromatography (50% ethyl acetate in hexanes) to provide 2.4 g (73% yield) of alcohol 2 as a white solid. $^1$H spectra of 2 agreed with the proposed structure.

C. Protection of 12-hydroxyl group

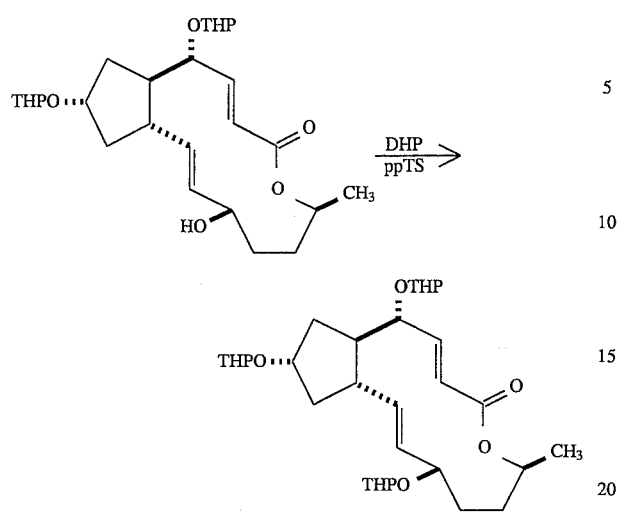

The 12-hydroxyl group of 2 is protected with a THP group as described in step A, above.

D. Conversion of Lactone to thiono-lactone

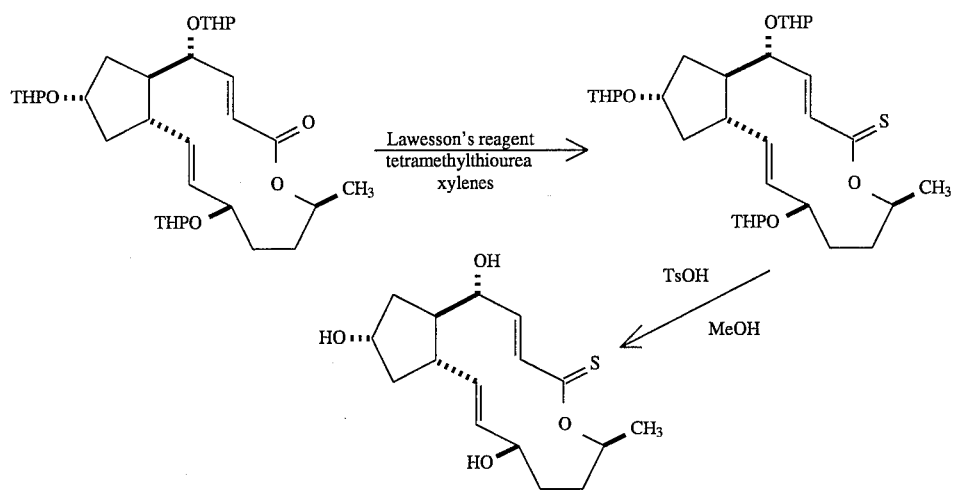

Conversion to the thiono-lactone is effected by the method of Step B in Example 1, followed by deprotection in 1% HCl in 95% EtOH as described in Step C of Example 1.

Example 3: Preparation of Thiono-lactone of (12S)-OH Brefeldin A by the following route:

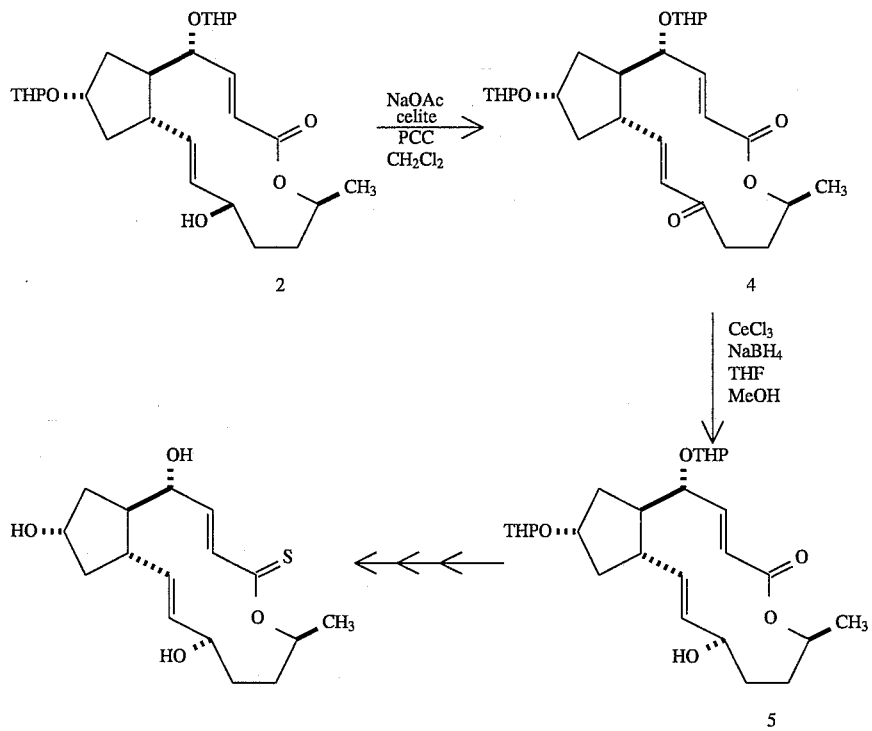

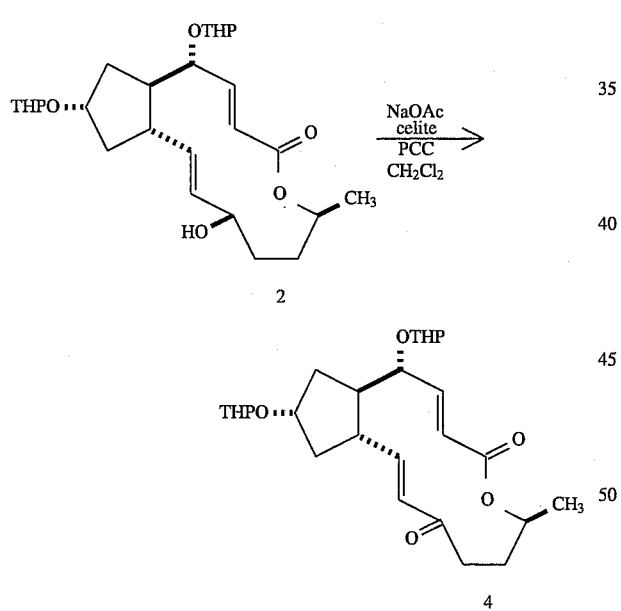

A. Oxidation

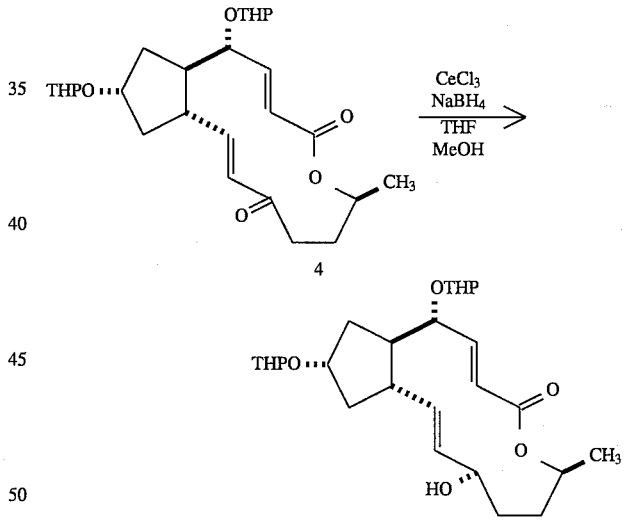

B. Stereospecific reduction

To a magnetically stirred solution of alcohol 2 (1.2 g, 2.6 mmol) in 26 mL of CH$_2$Cl$_2$ was added sodium acetate (320 mg, 3.9 mmol), celite (900 mg), and pyridinium chlorochromate (840 mg, 3.9 mmol). The reaction was stirred at room temperature for 4 h, then filtered through a bed of celite rinsing the solids with CH$_2$Cl$_2$ before concentrating. The crude product was purified via flash chromatography (50% ethyl acetate in hexanes) to provide 960 mg (81% yield) of ketone 4. $^1$H spectra of 4 agreed with the proposed structure.

To a magnetically stirred solution of ketone 4 (400 mg, 0.87 mmol) in 5 mL of THF and 12 mL of MeOH was added cerium (III) chloride (210 mg, 0.87 mmol) and stirred at room temperature for 25 min. The mixture was cooled to 0° C. and sodium borohydride (33 mg, 0.87 mmol) added. The reaction was stirred at 0° C. for another 5 min then warmed to room temperature and stirred for 20 min. The reaction was quenched with a 1:1 mixture of saturated aqueous NH$_4$Cl and H$_2$O and concentrated to remove the organic solvents. The aqueous residue was extracted with three portions of EtOAc. The combined organic extracts were dried over MgSO$_4$, filtered, and concentrated to afford 400 mg (quantitative yield) of alcohol 5. Compound 5 was judged sufficiently pure by $^1$H NMR analysis to be used in the subsequent reaction without further purification.

C. Thiono-lactone

The corresponding thiono-lactone may be obtained by protecting the 12-hydroxyl group of 5, reaction with Lawesson's reagent and deprotection as described in Steps C and D of the preceding example.

Example 4: Preparation of the thiono-lactone of 12,13 Dehydro-Brefeldin A by the following route:

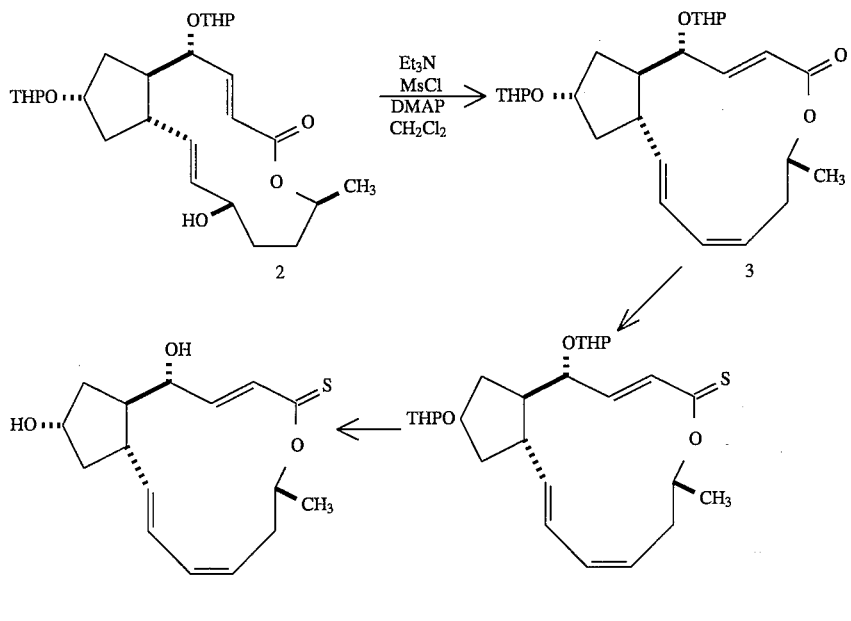

A. Elimination

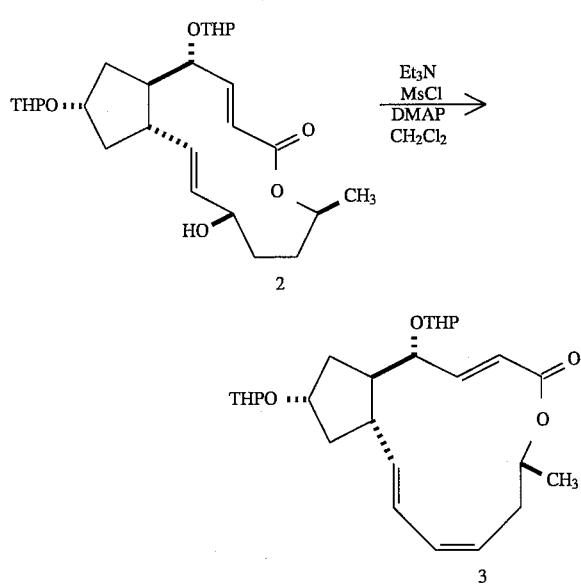

To a magnetically stirred solution of alcohol 2 (740 mg, 1.6 mmol) in 16 mL of $CH_2Cl_2$ at 0° C. was added triethylamine (490 μL, 3.5 mmol), 4-dimethylamino-pyridine (2.0 mg, 0.016 mmol), and methanesulfonyl chloride (190 μL, 2.4 mmol). The mixture was stirred at 0° C. for 1 h then warmed to room temperature and stirred another 30 min. The reaction was diluted with $CH_2Cl_2$ and washed with saturated aqueous $NaHCO_3$ and brine. The organic layer was dried over $MgSO_4$, filtered, and concentrated. The crude product was purified via flash chromatography (30% ethyl acetate in hexanes) to provide 630 mg (89% yield) of triene 3 as a white foam. $^1H$ spectra of 3 agreed with the proposed structure.

B. Conversion of 3 to the thiono-lactone

Compound 3 is converted to the protected thiono-lactone using Lawesson's reagent and deprotected by adaptation of the methods described in the preceding examples.

Example 5: Synthesis of Cyclopropyl derivative of BFA (II)

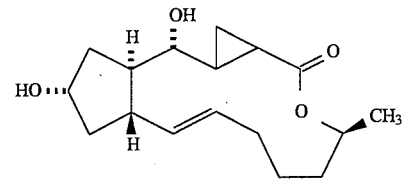

Trimethylsulfoxonium iodide (0.258 gram) was added to a 10 mL flask containing a stir bar, nitrogen inlet, 2.5 mL dimethyl sulfoxide (DMSO) and pentane washed NaH. The resulting slurry was stirred at room temperature until gas evolution ceased (15 minutes). Brefeldin A (0.107 gram) was added at once and stirring was continued for an additional hour at ambient temperature. The reaction mixture was quenched with water (4 mL) and extracted with ethyl acetate (4×50 mL). The combined organic extract was washed with water (2×25 mL), brine (25 mL) and dried over sodium sulfate. The solvent was removed under vacuum and the residue chromatographed through a silica gel column, eluted with ethyl acetate, to separate isomers.

The major R, R-isomer gave an oil which crystallized upon trituration with acetonitrile. Recrystallization from acetonitrile gave crystals suitable for x-ray crystallography. The structure was consistent with the R, R-isomer as determined by x-ray crystallography and the following $^1H/^{13}C$ NMR data:

$^1H$ NMR $(CDCl_3)$ppm 1.0 (d,2H, Me) 1.1–1.65(m, 8H) 1.7–2.25(m,10H) 3.5(d,1H,C(4)H̲—OH) 4.15(m,1H, C(7)H̲—OH) 4.9(m,1H, C(15)H̲—OR) 5.3 (m,2H, C(10)H̲=C(11)H̲)

$^{13}$C NMR (CDCl$_3$) ppm 173.9, 137.1, 129.4, 73.1, 72.6, 69.6, 50.4, 44.9, 44.1, 41.1, 34.2, 30.1, 26.2, 25.1, 20.6, 15.9, 11.1.

The minor S,S-isomer was isolated as an oil. The S,S-isomer structure was consistent with the following $^1$H/$^{13}$C NMR data:

$^1$H NMR (CDCl$_3$) ppm 0.75(m,1H) 1.08(d, 2H, CH$_3$) 1.1–1.2(m,1H) 1.25–1.4(m, 5H) 1.55(m, 1H) 1.7(m, 1H) 1.8–2.2(m, 8H) 2.3(m, 1H) 3.7(m, 1H) 4.2 (m, 1H) 4.8(d, 1H) 5.3(m, 2H)

$^{13}$C NMR (CDCl$_3$) ppm 12.5, 18.0, 22.0, 23.7, 25.7, 32.5, 35.7, 38.9, 42.9, 43.7, 49.2, 68.0, 71.8, 81.5, 131.4, 133.6, 176.8.

Example 5. Preparation of thiono-lactones of the cyclpropyl derivatives

Examples 1, 2 and 3 may be carried out using Compound II (R,R, S,S or a mixture of the two) in place of BFA to yield the corresponding 12-hydroxy and triene thiono-lactones bearing a 2,3 cyclopropyl group.

Example 6: Guanine Nucleotide Exchange Factor Assay

Recombinant myristoylated ADP-ribosylation factor (ARF) is purified from *Escherichia coli* co-expressing the human ARF-1 gene and N-myristoyltransferase as described in Weiss, O., et al., J. Biol. Chem., 264:21066–21072 (1989) and Duronio, R. J., et al., Proc. Natl. Acad. Sci. USA, 87:1506–1510 (1990).

Golgi membranes from rat livers are obtained by sucrose gradient centrifugation as described in Balch, W. E., et al., Cell, 39:525–536 (1984).

Incubations are carried out as described in Donaldson, J. G., et al., Nature 360:350–352 (1992) and Helms, J. B., and Rothman, J. E., Nature 360:352–354 (1992). Briefly, a 50.5 µl reaction mixture containing ARF, Golgi membranes, sucrose, ovalbumin, HEPES-KOH buffer containing KCl and Mg, 100 µM compound and [$^{35}$S]GTP is incubated at 37° C. for 15 minutes. The specific reactions are set up with 5 µl of 2.3M sucrose, 10 µl of 0.5 mM compound (except for the background and control reactions, in which no compound is added), 5 µl buffer, 5 µl of 16 mg/ml Ovalbumin, 5 µl of 0.6 mg/ml golgi (none in background run), 8 µl of 0.4 gm/ml Arf-1 (except none in background run) and 12.5 µl of 20 µM GTP ($^{35}$S), with the background and control reactions diluted with 23 µl and 10 µl, respectively, of water.

The amount of ARF-bound and -unbound [$^{35}$S]GTP is separated with 10 kD molecular weight cutoff cellulose filters. Nonspecific binding (from background run) is subtracted.

Alternatively, the ARF-bound [$^{35}$S]GTP can be separated by Sephadex G25 gel filtration.

Example 7: Test for Antiviral Activity

The antiviral activity and cytotoxic microscopic effects of our compounds may be determined in the following manner.

Hep2 cells in RPMI/1640 medium with 5% fetal calf serum are grown to provide a confluent sheet of cells. Various concentrations of the compound(s) to be tested, as well as positive and negative controls, are added. The cells are then incubated at 37° C., in 5% carbon dioxide.

In a cytotoxicity screening assay, different concentrations of the compound(s) to be tested, as well as positive and negative controls, are added to the cell culture. Cytotoxicity is determined by microscopic examination on days 3 and 6.

The antiviral and cytotoxic effects of the compounds on Hep2 cells infected with HSV-1 can be determined as follows.

Hep2 cells in RPMI/1640 medium with 5% fetal calf serum are added to microtiter wells and incubated at 37° C. in 5% carbon dioxide. To the Hep2 cells, various concentrations (4 wells/concentration compound) of the compound(s) to be tested, as well as positive and negative controls, are added. Typical test concentrations may run from about 0.1–50 µg/ml. HSV-1 virus is added 7 hours later. The cell culture specimens are examined for evidence of viral growth and Hep2 microscopic toxicity on days 1, 2, 3, 4, 5, 6, 7 and 10 post-infection. Virus controls at dilutions of $10^{-10}$ to $10^{-14}$ are included.

Example 8: In vivo Toxicity Study

An intraperitoneal dose response study of the compounds of this invention can be carried out in mice to provide toxicological data as follows.

Female CD-1 mice (6/group) are employed in this investigation. The compound is suspended in 0.5% carboxymethylcellulose (CMC). The animals are scheduled to receive the compound, intraperitoneally, at dosage levels of 50, 100 and 400 mg/kg/day for 5 consecutive days. All doses are administered in a constant volume of 20 ml/kg. Another group of animals receives 0.5% CMC (20 ml/kg) and serves as a control. The animals are then observed for at least two weeks after which a necropsy is performed. Tissues are collected for histopathologic evaluation.

Example 9. Preparation of 7-succinyl Brefeldin A:

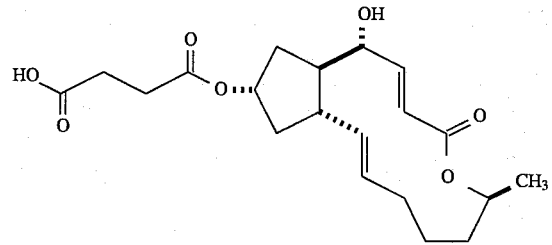

A flask fitted with a reflux condenser, stir bar, and nitrogen inlet was charged with brefeldin A (1.8 mMoles), succinic anhydride (1.9 mMole) methylene chloride (15 mL) and toluene sulfonic acid (catalytic). The turbid solution was refluxed for 16 hours. The resulting clear solution was transfered to a separatory funnel and the organic layer was water washed two times. The organic layer was dried over sodium sulfate, filtered and concentrated under vacuum to a heavy oil. The oil was subjected to high vacuum, and a rigid foam resulted. The foam was triturated with acetonitrile and filtered. The amorphous solid was dried in a vacuum oven at 40° C. to a constant weight (1.35 mMoles).

Both $^{13}$C and $^1$H nmr spectra agreed with the anticipated structure.

| HPLC: C-18 | |
| --- | --- |
| flow | 0.7 mL/min |
| | Acetonitrile/water 60/40 |
| det | 220 nm |
| R$_T$ | 11.6 min. (brefeldin A 8.6 min) |

We claim:
1. A compound of the formula:

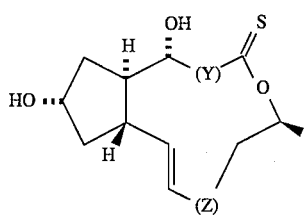
wherein Y is a carbon-carbon (trans) double bond or a cyclopropyl ring and Z is
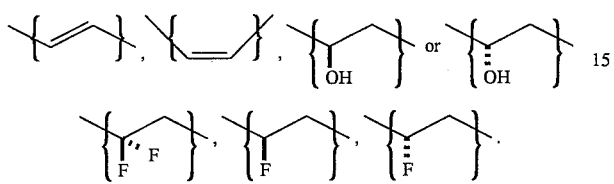
2. A compound of claim I of the formula:
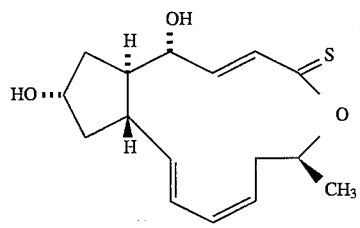
or
3. A compound of claim I of the formula:
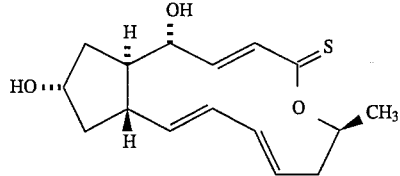
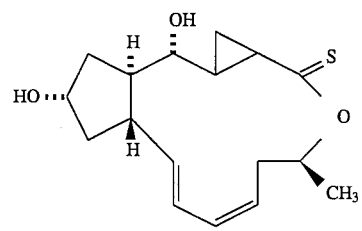
or
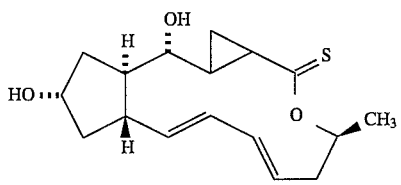
* * * * *